United States Patent [19]
Fox

[11] Patent Number: 5,879,684
[45] Date of Patent: Mar. 9, 1999

[54] SKIN TIGHTENING FORMULATION AND METHOD FOR TREATING SKIN

[75] Inventor: Charles Fox, Fair Lawn, N.J.

[73] Assignee: Hydron Technologies, Inc., Boca Raton, Fla.

[21] Appl. No.: 840,208

[22] Filed: Apr. 11, 1997

Related U.S. Application Data

[60] Provisional application No. 60/016,250, Apr. 19, 1996.
[51] Int. Cl.[6] ........................ A61K 35/78; A61K 39/385
[52] U.S. Cl. ..................................... 424/195.1; 424/78.03; 514/848; 514/944
[58] Field of Search ..................................... 514/848, 944; 424/78.03, 195.1

[56] References Cited

U.S. PATENT DOCUMENTS

| | | | |
|---|---|---|---|
| 4,911,925 | 3/1990 | Shatkina et al. | 424/401 |
| 5,091,171 | 2/1992 | Yu et al. | 424/642 |
| 5,385,938 | 1/1995 | Yu et al. | 514/557 |
| 5,422,370 | 6/1995 | Yu et al. | 514/557 |

*Primary Examiner*—Leonard Schenkman
*Attorney, Agent, or Firm*—Dorsey & Whitney LLP

[57] ABSTRACT

A skin tightening aqueous gel formed from the combination of water, a dispersed finely particulate vegetable based tautening or tensor agent, a polymeric gelling agent, a liquid hydrocarbon dispersing aid and a nonionic surfactant.

There is described a method of dispensing and spreading the gel onto skin areas for the tightening treatment.

41 Claims, No Drawings

SKIN TIGHTENING FORMULATION AND METHOD FOR TREATING SKIN

RELATED PATENT APPLICATIONS

This application claims the benefit of the filing date of copending provision application Ser. No. 60/016250, filed Apr. 19,1996

BACKGROUND TO THE INVENTION

In mankind's eternal search for the fountain of youth, more and more attention has been directed to developing compositions that eliminate, shrink, or mask wrinkles and other unsightly lines in the skin. Many products along these lines are known in the art.

For example, cosmetics have long included humectants, which absorb or retain moisture. These cosmetics may have the effect of temporarily smoothing out wrinkles because the skin swells where the humectant is applied. Other products have been developed to tighten skin upon application of the product. Among these products are tensors. The tensors are typically proteinaceous in character and form a film on the skin surface. The protein retracts upon drying to tighten the skin and temporarily remove wrinkles.

Many of the early products were serum-based. These products provided localizing and temporary tightening of the skin. However, the movement in the industry is away from animal-based products to vegetable and fruit-based products.

Due to this movement, the use of alpha-hydroxy acids for the purposes of wrinkle removal has gained considerable popularity. The use of alpha-hydroxy acids is not new. For example, German Patent Nos. 1,263,987 to Schlenger and 2,703,189 to Higer et al. disclose the addition of various ingredients, including alpha-hydroxy containing materials, to cosmetic formulations. These compounds have also gained favor in the United States. For example, U.S. Pat. Nos. 5,091,171, 5,385,938 and 5,422,370 to Yu et al. disclose the same use of alpha-hydroxy acids.

Because these products are applied to the skin, the products should be smooth and luxurious to the touch. The products should exhibit smooth and non-gummy rubout characteristics. Furthermore, the products should not be grainy or aesthetically unappealing.

The products in the prior art typically suffer from the fact that the ingredients most effective for skin moisturization or wrinkle reduction generally are solids that have poor stability and are immiscible in the liquid vehicles most desired for application of the ingredients to the skin. In addition, these ingredients typically give a grainy texture to the products.

There is a need for delivery vehicle that avoids these problems and provides a smooth and creamy vehicle for delivery of skin tighteners to the skin.

It is an object of the present invention to provide a delivery system for skin tightener agents that is smooth and non-grainy to the touch and exhibits smooth and non-gummy rubout characteristics It is another object of the present invention to provide a delivery system that is aesthetically pleasing.

It is yet another object of the present invention to provide a delivery system for vegetable based tightening agents that is shelf stable.

These and other objects and advantages of the present invention will become apparent with reference to the following specification.

THE INVENTION

This invention relates to a skin tautening aqueous gel. It is formed from the combination of water, a dispersed finely particulate vegetable based tautening or tensor agent containing a protein-based complex of vegetable extract and polysaccharides, a polymeric gelling agent, a liquid hydrocarbon dispersing aid and a nonionic surfactant that maintains the dispersion of the liquid hydrocarbon dispersing aid in the gel.

The gel of the invention has exceptional storage stability without settling of solid components therein, thereby maintaining the effectiveness of the composition for skin tautening over extended periods of time, e.g., months, years. Clinical tests show that, when used nightly, the gel of the invention produced significantly improved cosmetic results within eight weeks, including a 30% reduction in the appearance of fine facial lines, a 35% increase in hydration, a 21% increase in skin firmness, and progressive improvement in skin's resilience and elasticity.

The dispersed finely divided vegetable based tautening or tensor agent employed in the aqueous gel of the invention may be any of the commercially available protein-based complexes of vegetable extract and polysaccharides for this purpose. Alban Muller International sells an example of a suitable tensor under the trademark VEGETENSOR. This tensor comprises a protein based complex of Pea (Pisum sativum) and Sclerotium Gum.

The polymeric gelling agent may be any of the acrylic polymers sold for this purpose that will form gels on admixture with water. Illustrative of such agents are the carbomers and the polyacrylamides. Illustrative are the carbomers are the Carbopol® resins sold by B. F. Goodrich Company. Seppic, Inc. of Fairfield, N.J. sells an example of a suitable polyacrylamide under the trademark SEPIGEL 305. This gelling agent contains with the polyacrylamide, a $C_{13}$–$C_{14}$ isoparaffin hydrocarbon dispersing aid and a nonionic surfactant.

The gel of the present invention is creamy and smooth to the touch. It is not greasy and has excellent rubout characteristics. The gelling agent maintains the tautening agent as a dispersion that is stable. Furthermore, this delivery vehicle allows control of the delivery of the tautening agent over the skin.

DETAILS OF THE INVENTION

The present invention is a skin tautening aqueous gel formed from the combination of water, a dispersed finely particulate vegetable based tautening agent, a polymeric gelling agent, a liquid hydrocarbon dispersing aid and a nonionic surfactant that maintains the dispersion of the dispersing aid in the gel. The gel of the present invention is creamy and smooth to the touch. It is not greasy and has excellent rubout characteristics. The gelling agent maintains the tautening agent in a dispersion that is stable. Furthermore, this delivery vehicle allows control of the product as applied over the skin.

As indicated above, VEGETENSOR, made and sold by Alban Muller International, is a suitable tensor. This tensor comprises a protein-based complex of Pea (Pisum sativum) and Sclerotium Gum. The pea protein is filmogeneous and is well suited to use in creams, lotions, and the like. Once applied, the dried product retracts, thereby lending the tensor, or skin tightening, effect. It is believed that these properties enhance the apparent cosmetic effects that the gel has on the skin. It is possible that the proteins contribute amino acids to the skin, thereby stimulating skin regeneration.

While vegetable based tensors are preferred, they may pose a delivery problem because they typically exhibit low solubility in preferred delivery vehicles. The result is that the tensor will have a tendency to settle out of the delivery vehicle within which it is contained. This results in low stability of the skin product. Consequently, the tensors typically lend a grainy texture to the skin product. The tensors with settle out of the matrix in which they are dispersed after a period of time, leaving a clear layer on top of the preparation.

Use of a tautening agent such as VEGETENSOR therefore requires the use of an appropriate formulation to avoid phase separation. It has been found that a gelling agent in combination with appropriate emollients keeps the VEGETENSOR from settling out of (precipitating from) an aqueous gel dispersion. The addition of an appropriate gelling agent aids in stabilizing the finely dispersed tautener in water. The resulting gel possesses excellent non-gummy rubout characteristics, minimal tackiness (not sufficient to restrain flow on the skin), as well as a luxuriant hand without stringiness, when spread over skin, especially to facial skin areas. To the extent that the tensor is not fully soluble in the water forming the gel, that which is not fully solubilized is finely and stably dispersed within the gel.

Gels that are made from hydrogen bonding water with an acrylic polymer typically form tacky and stringy materials that are difficult to handle and are certainly less than is desirable to place on skin. This invention eliminates such characteristics in the typical aqueous gel by dispersing fine droplets of a hydrophobic hydrocarbon oil in the gel and maintaining it in the gel in a discrete state by the inclusion of a nonionic surfactant.

The addition of a liquid hydrocarbon dispersant and a nonionic surfactant in the formulation of the gel serves to eliminate tackiness. How it does this is not fully understood, but it is believed the dispersant interferes with polymeric hydrogen bonded chains by physically placing small incompatible droplet in the gel that break up the degree of hydrogen bonding that is necessary for stringiness. The resulting gel is smooth to the touch and has a glossy shine that is pleasing to the eye.

Additional benefits may obtain to the present invention. For example, many tightening agents also retain water, thereby lending moisturizing characteristics to the composition. Furthermore, the vegetable proteins in the tightening agents may lend amino acids to skin, thereby generating elastin and collagen formation.

Gelling agents or binders are traditionally added to the water-based cosmetics to help in stabilizing the formulation and preventing separation of the liquid from the solid phases. In this case, the addition of an appropriate gelling agent maintains the dispersed tensor and eliminates or minimizes these separation problems. The agent forms effective gels with these tightening agents and therefore maintains the stability of the product for a substantial period of time.

Gelation is accomplished according to this invention by the interaction of water and the gelling agent. There are a number of effective gelling aids used in forming a cosmetic gel. Polyacrylamides represent a class of gelling aid. Illustrative of the polyacrylamide is the following recurring structure:

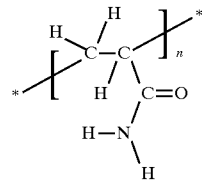

Such polyacrylamides are typically macropolymers and may have a weight average molecular weight greater that about 50,000, preferably greater than about 100,000, to as high as 3,000,000.

Carbomers represent another class of gelling aid. The carbomers are typically defined as high molecular weight polymers based on acrylic acid crosslinked with allyl sucrose. Variations of such copolymers are also termed carbomers. The carbomers provide high yield values and thus are very effective suspending agents. The carbomers have extremely high molecular weights ranging from about 700,000 to about 5,000,000. Illustrative of such carbomers are the Carbopol® water soluble acrylic acid polymers sold by B. F. Goodrich Specialty Chemicals characterized by the following recurring structure:

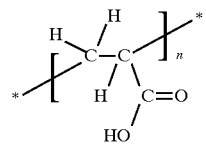

Suitable Carbopol® water soluble acrylic acid polymers include Carbopol 910, 941, 934, 924P and 940. Carbopol 934P and 940, because of their abilities to thicken with low concentrations of the polymer, are preferred. Other gelling aids are nonionic surfactants. These thickening agents are typically used in amounts less than about 1 weight percent of the weight of the cosmetic formulation of the invention. However, the viscosity, rheology and thixotropy of the resulting formulation govern the amount of the thickener used in the formulation. Thus, the amount of the thickener should be coordinated with the amount of the water and the amount of the solids in the formulation to achieve the desired viscosity and assure the thixotropic flow qualities of the formulation. On the whole, the formulation will employ more than about 0.1 weight percent of the gelling agent component.

In addition to the carbomers and polyacrylamides, one may use, alone or in combination with them, typical thixotropic agents used in cosmetic formulations. Illustrative of such thixotropic agents are the natural gums, including gum traganth and gum karaya, the seaweed colloids such as various carageenans, extracts of Irish moss, and sodium alginate, the synthetic celluloses including hydroxyethyl cellulose, sodium carboxymethyl cellulose and methyl cellulose, and mineral colloids such as bentonite. They alone are typically ineffective in combination with water in forming the gel formulation of this invention.

A preferred polyacrylamide gelling agent is SEPIGEL 305. This product comprises polyacrylamide, and includes a liquid $C_{13-14}$ branched chain hydrocarbon dispersant (e.g., $C_{13-14}$ isoparaffin) and the nonionic surfactant as Laureth-7. Laureth-7 is the ethoxylate of lauryl alcohol or a mixture of alcohols having an average of 12 carbon atoms. This product is typically used as a thickening agent for emulsions. Gels may be obtained by simply adding water to this product. The product has excellent cosmetic properties that gives a soft, non-sticky feel and smooth consistency in a gel containing the vegetable tensor solids.

The polyacrylamide resins hydrogen bond with water and such forms a framework that maintains the vegetable tensor particles suspended. As long as the gel maintains its viscosity, the tensor particles are kept from separating and settling.

The isoparaffin acts, in effect, as a lubricant. Isoparaffin gives the polyacrylamide better flow characteristics. The isoparaffin tends to break the polyacrylamide into discrete gel particles. Consequently, the polyacrylamide gel loses its stickiness. In the general practice of the invention, the liquid hydrocarbon dispersing aid may be a liquid branched chain hydrocarbon containing from about 10 to about 15 carbon atom, preferably from about 12 to about 14 carbon atoms. Branching assure that the hydrocarbon is a liquid over a greater temperature range, thereby assuring better dispersion properties over a broader temperature range for the gel in which the dispersing aid is added.

However, a $C_{13-14}$ isoparaffin is not easily dispersed in a gel of this nature. A surfactant dispersing-agent, such as Laureth-7, is employed to assure such dispersion. Laureth-7 is an ethylene oxide adduct of lauryl alcohol that can be formed by the reaction of ethylene oxide with lauryl alcohol or a mixture of alcohols that has an average carbon content of about 12 carbon atoms, in the presence of a catalyst. Acidic or basic compounds typically serve as the catalyst. The adduct acts as a nonionic surfactant that helps maintain the integrity of the dispersed isoparaffin. In addition, Laureth-7 like any surfactant provides good slip properties to the formulation and such aids in the application of the gel. Other liquid hydrocarbons can be employed in place of the isoparaffin and other nonionic surfactants can be used in place of Laureth-7.

It is contemplated that other gelling agents can be used, such as mixtures of SEPIGEL 305 and CAROPOL 934P or 940.

An example of a formula (in percent by weight) for the skin tightening gel follows:

TABLE I

| Ingredients | Percent (wt. %) | |
|---|---|---|
| | Range | Preferred |
| Deionized Water | 65–85 | 76.24 |
| Hydroxyethyl Cellulose | 0.4–1.2 | 0.70 |
| VEGETENSOR | 2.00–4.00 | 3.00 |
| Disodium EDTA | 0.1–0.3 | 0.20 |
| Butylene Glycol (and) Algae Extract | 2.50–7.5 | 5.00 |
| Polysaccharide (and) Casein Hydrolyzate | 1.0–8.0 | 5.00 |
| Sodium Hyaluronate (1%) | 2.0–7.0 | 5.00 |
| Sepigel 305 | 0.5–4.5 | 2.00 |
| Saccharide Isomerate | 0–2.5 | 1.00 |
| Diazolidinylurea (and) Methylparaben (and) Polyparaben | 0–2.0 | 1.00 |
| Propylene Glycol | 0–1.5 | 0.50 |
| Sodium PCA | 0–0.75 | 0.25 |
| Polyglyceryl Methacrylate | 0–0.75 | 0.10 |
| HYDRON Solution 931-48A | 0–0.75 | 0.01 |

It is contemplated that fragrances and dyes may be added. For example, Green floral fragrance and D&C Red No. 33 (1% aq. sol.) could be added (comprising 0.10% and 0.10% of the composition, respectively). A particularly preferred formulation comprises the following:

TABLE II

| Ingredients | Percent (wt. %) | |
|---|---|---|
| | Range | Preferred |
| Deionized Water | 65–85 | 69.84 |
| Hydroxyethyl Cellulose | 0.4–1.2 | 0.70 |
| VEGETENSOR | 0.01–4.00 | 0.50 |
| Disodium EDTA | 0.1–0.35 | 0.24 |
| Glycerin | 0–20.00 | 10.00 |
| Butylene Glycol (and) Algae Extract | 2.50–7.5 | 5.00 |
| Polysaccharide (and) Casein Hydrolyzate | 1.0–8.0 | 5.00 |
| Sodium Hyaluronate (1%) | 2.0–7.0 | 5.00 |
| Sepigel 305 | 0.5–4.5 | 1.00 |
| Dimethicone Copolyol Isostearate (Silwax WD-IS, Siltech) | 0.0–1.0 | 0.01 |
| PEG-20 Methyl Glucose Sesquistearate (Glucamate SSE-20, Amerchol) | 0.0–1.0 | 0.01 |
| Polysorbate 40 | 0.0–1.0 | 0.01 |
| Polysorbate 60 | 0.0–1.0 | 0.01 |
| Polypropylene Glycol (Polyglycol P425, Dow Chemical) | 0.0–1.0 | 0.01 |
| Green Floral Fragrance (Hagelin 805872/water dispersible) | 0.0–5.0 | 0.23 |
| D & C Red No. 33 (0.1% aq. sol.) | 0.0–2.0 | 0.10 |
| Polaxamer 184 (Pluracare L64, BASF) | 0.0–1.0 | 0.01 |
| Steareth-20 (Brij 78, ICI Americas) | 0.0–1.0 | 0.01 |
| Saccharide isomerate | 0–2.5 | 1.00 |
| Propylene Glyco and Diazolidinylurea (and) Methylparaben (and) Polyparaben (Germaben II, ISP Sutton) | 0–2.0 | 1.00 |
| Sodium PCA | 0–0.75 | 0.23 |
| Polyglyceryl Methacrylate (Lubrajel Oil, Amerchol) | 0–0.75 | 0.08 |
| HYDRON Solution 931-48A | 0–0.75 | 0.01 |
| Total | | 100 |

The hydroxyethyl cellulose is commercially available under the trademark NATROSOL 250, sold by Aqualon.

Disodium EDTA is a stabilizer.

The butylene glycol (and) Algae Extract product is commercially available under the trademark APT from Centerchem, Inc. of Stamford, Conn. The product is bio-engineered from a strain of red marine algae (Ahnfeltia concinna). This product lends moisturizing and hydration qualities to the gel. It is believed that this product functions with the polysaccharides in the gel to enhance moisturization, soothing and aesthetic characteristics.

The polysaccharide (and) casein hydrolyzate product is commercially available under the trademark PENTACARE HP from Centerchem, Inc. of Stamford, Conn. This product forms a fine humectant film over the skin when applied that resists cracking or flaking. It has skin tightening characteristics.

Saccharide Isomerate is commercially available under the trademark PENTAVITIN from Centerchem, Inc. of Stamford, Conn. This product is similar to carbohydrate complexes that are found in the stratum corneum of the skin. This product binds to the skin and has moisture retention benefits.

Sodium PCA is sodium DL-2-pyrrolidone-5-carboxylate and is commercially available under the trademark AJIDEW N-50 from Anjinomoto Co., Inc. of Tokyo, Japan. The Sodium PCA is a natural humectant and is extremely hygroscopic.

Polyglyceryl Methacrylate is available under the trademark LUBRAJEL OIL from Amerchol.

Hydron Solution 931-48A is available from Hydron Technologies, Inc. of Boca Raton, Fla. The Solution is based on an hydroxyethyl methacrylate homopolymer. The Solution forms on the skin a discontinuous film protective layer that is water impermeable and highly pliable. The film conforms to the contortions and convolutions of the skin. It has the desirable effect of lending the characteristic of cosmetic permanency on the skin surface due to its moisture resistance.

A method of making the composition follows:

Heat the water to 65°–70° C. Disperse the NATROSOL 250 in the water using a high shear stirrer. After dispersing the NATROSOL 250, disperse the VEGETENSOR in the water and continue high shear stirring until the temperature drops to 50° C. Homogenize the batch until the mixture is smooth.

With continuous stirring, add the remaining ingredients. At this point, the mixture thickens and a gate mixer may be required to continue stirring. Once all of the ingredients have been added, homogenize the batch again for approximately thirty minutes and cool to ambient temperature.

The preferred formulation may flake after application of the composition to skin. To alleviate the flaking, more plasticizer may be added. In this regard, glycerol may be added instead of propylene glycol. It is believed that glycerol is not as readily absorbed by the skin as is the propylene glycol.

The formulation is applied to the skin by hand, brush, pad, and the like, as a thin film spread over the skin surface area that the individual desires to cosmetically effect skin tautening. Because the formulation of the invention is a non-greasy gel that is easily and efficiently rubbed into the skin, a dab of the gel formulation is place in the area of treatment. The dab is then rubbed by hand or with a brush, pad or other device, into a thin film that is spread over a greater area of treatment, and with constant rubbing of the area, the formulation is imbibed into the outer skin layer and skin tightening results.

For maximum long-term benefits, the gel of this invention is used each night typically on the user's face, after cleansing and moisturizing the face. The gel is spread sparingly with the user's or another's fingertip(s) on the sections of the face that such cosmetic treatment is desired. The user concentrates the gel on existing facial lines and areas where signs of aging show earliest. The area where the gel is applied is pat gently until the gel is completely absorbed by the skin. Also, the gel may be used at any time of day as a quick lift to temporarily firm, and soften the look of fine facial lines. The gel can be worn alone or with makeup. For example, the gel may be dabbed lightly over a liquid foundation and applied under powder after the foundation has completely dried.

I claim:

1. A skin tautening aqueous gel comprising a homogeneous blend of water, a dispersed finely particulate vegetable based tensor agent containing a protein-based complex of vegetable extract and polysaccharides, a polymeric gelling agent, a liquid hydrocarbon dispersing aid and a nonionic surfactant that maintains the dispersion of the liquid hydrocarbon dispersing aid in the gel.

2. The skin tautening aqueous gel of claim 1 wherein the tensor agent comprises a protein-based complex of Pea and Sclerotium Gum.

3. The skin tautening aqueous gel of claim 1 wherein the polymeric gelling agent is a polyacrylamide.

4. The skin tautening aqueous gel of claim 2 wherein the polymeric gelling agent is a polyacrylamide.

5. The skin tautening aqueous gel of claim 1 wherein the polymeric gelling agent is a carbomer.

6. The skin tautening aqueous gel of claim 2 wherein the polymeric gelling agent is a carbomer.

7. The skin tautening aqueous gel of claim 1 wherein the polymeric gelling agent is a mixture of a polyacrylamide and a carbomer.

8. The skin tautening aqueous gel of claim 2 wherein the polymeric gelling agent is a mixture of a polyacrylamide and a carbomer.

9. The skin tautening aqueous gel of claim 1 wherein the liquid hydrocarbon dispersing aid is a liquid branched chain hydrocarbon containing from about 10 to about 15 carbon atoms.

10. The skin tautening aqueous gel of claim 9 wherein the liquid hydrocarbon dispersing aid is a liquid branched chain hydrocarbon containing from about 12 to about 14 carbon atoms.

11. The skin tautening aqueous gel of claim 10 wherein the liquid hydrocarbon dispersing aid is a $C_{13-14}$ isoparaffin.

12. The skin tautening aqueous gel of claim 1 wherein the nonionic surfactant is an ethylene oxide adduct of lauryl alcohol or a mixture of alcohols that has an average carbon content of about 12 carbon atoms.

13. The skin tautening aqueous gel of claim 2 wherein the nonionic surfactant is an ethylene oxide adduct of lauryl alcohol or a mixture of alcohols that has an average carbon content of about 12 carbon atoms.

14. The skin tautening aqueous gel of claim 3 wherein the nonionic surfactant is an ethylene oxide adduct of lauryl alcohol or a mixture of alcohols that has an average carbon content of about 12 carbon atoms.

15. The skin tautening aqueous gel of claim 4 wherein the nonionic surfactant is an ethylene oxide adduct of lauryl alcohol or a mixture of alcohols that has an average carbon content of about 12 carbon atoms.

16. The skin tautening aqueous gel of claim 9 wherein the nonionic surfactant is an ethylene oxide adduct of lauryl alcohol or a mixture of alcohols that has an average carbon content of about 12 carbon atoms.

17. The skin tautening aqueous gel of claim 10 wherein the nonionic surfactant is an ethylene oxide adduct of lauryl alcohol or a mixture of alcohols that has an average carbon content of about 12 carbon atoms.

18. The skin tautening aqueous gel of claim 11 wherein the nonionic surfactant is an ethylene oxide adduct of lauryl alcohol or a mixture of alcohols that has an average carbon content of about 12 carbon atoms.

19. The skin tautening aqueous gel of claim 1 wherein the blend contains a butylene glycol Algae Extract.

20. The skin tautening aqueous gel of claim 2 wherein the blend contains a butylene glycol Algae Extract.

21. The skin tautening aqueous gel of claim 3 wherein the blend contains a butylene glycol Algae Extract.

22. The skin tautening aqueous gel of claim 4 wherein the blend contains a butylene glycol Algae Extract.

23. The skin tautening aqueous gel of claim 5 wherein the blend contains a butylene glycol Algae Extract.

24. The skin tautening aqueous gel of claim 6 wherein the blend contains a butylene glycol Algae Extract.

25. The skin tautening aqueous gel of claim 7 wherein the blend contains a butylene glycol Algae Extract.

26. The skin tautening aqueous gel of claim 8 wherein the blend contains a butylene glycol Algae Extract.

27. The skin tautening aqueous gel of claim 9 wherein the blend contains a butylene glycol Algae Extract.

28. The skin tautening aqueous gel of claim 10 wherein the blend contains a butylene glycol Algae Extract.

29. The skin tautening aqueous gel of claim 11 wherein the blend contains a butylene glycol Algae Extract.

30. The skin tautening aqueous gel of claim 12 wherein the blend contains a butylene glycol Algae Extract.

31. The skin tautening aqueous gel of claim 13 wherein the blend contains a butylene glycol Algae Extract.

32. The skin tautening aqueous gel of claim 14 wherein the blend contains a butylene glycol Algae Extract.

33. The skin tautening aqueous gel of claim 15 wherein the blend contains a butylene glycol Algae Extract.

34. The skin tautening aqueous gel of claim 16 wherein the blend contains a butylene glycol Algae Extract.

35. The skin tautening aqueous gel of claim 17 wherein the blend contains a butylene glycol Algae Extract.

36. The skin tautening aqueous gel of claim 18 wherein the blend contains a butylene glycol Algae Extract.

37. The skin tautening aqueous gel of claim 1 wherein the blend contains the following formulation:

| | Percent by weight: |
|---|---|
| Deionized Water | 65–85 |
| Hydroxyethyl Cellulose | 0.4–1.2 |
| A protein complex of Pea (*Pisum sativum*) and Sclerotium Gum | 2.00–4.00 |
| Disodium EDTA | 0.1–0.3 |
| Butylene Glycol (and) Algae Extract | 2.50–7.5 |
| Polysaccharide (and) Casein Hydrolyzate | 1.0–8.0 |
| Sodium Hyaluronate (1%) | 2.0–7.0 |
| Polyacrylamide gelling agent | 0.5–4.5 |
| Saccharide Isomerate | 0–2.5 |
| Diazolidinylurea (and) Methylparaben (and) Polyparaben | 0–2.0 |
| Propylene Glycol | 0–1.5 |
| Sodium PCA | 0–0.75 |
| Polyglyceryl Methacrylate | 0.–0.75 |
| A hydroxyethyl methacrylate homopolymer solution | 0–0.75 |

38. The skin tautening aqueous gel of claim 37 wherein the blend contains the following formulation:

| | Percent by weight: |
|---|---|
| Deionized Water | 76.24 |
| Hydroxyethyl Cellulose | 0.70 |
| A Protein complex of Pea (*Pisum sativum*) and Sclerotium Gum | 3.00 |
| Disodium EDTA | 0.20 |
| Butylene Glycol (and) Algae Extract | 5.00 |
| Polysaccharide (and) Casein Hydrolyzate | 5.00 |
| Sodium Hyaluronate (1%) | 5.00 |
| Polyacrylamide gelling agent | 2.00 |
| Saccharide Isomerate | 1.00 |
| Diazolidinylurea (and) Methylparaben (and) Polyparaben | 1.00 |
| Propylene Glycol | 0.50 |
| Sodium PCA | 0.25 |
| Polyglyceryl Methacrylate | 0.10 |
| A hydroxyethyl methacrylate homopolymer solution | 0.01 |

39. The skin tautening aqueous gel of claim 1 wherein the blend contains the following formulation:

| | Percent by weight: |
|---|---|
| Deionized Water | 65–85 |
| Hydroxyethyl Cellulose | 0.4–1.2 |
| A protein complex of Pea (*Pisum sativum*) and Sclerotium Gum | 0.01–4.00 |
| Disodium EDTA | 0.1–0.35 |
| Glycerin | 0–20.00 |
| Butylene Glycol (and) Algae Extract | 2.50–7.5 |
| Polysaccharide (and) Casein Hydrolyzate | 1.0–8.0 |
| Sodium Hyaluronate (1%) | 2.0–7.0 |
| Polyacrylamide gelling agent | 0.5–4.5 |
| Dimethicone Copolyol Isostearate | 0.0–1.0 |
| PEG-20 Methyl Glucose Sesquistearate | 0.0–1.0 |
| Polysorbate 40 | 0.0–1.0 |
| Polysorbate 60 | 0.0–1.0 |
| Polypropylene Glycol | 0.0–1.0 |
| Green Floral Fragrance | 0.0–5.0 |
| Red dye (0.1% aq. sol.) | 0.0–2.0 |
| Saccharide Isomerate | 0–2.5 |
| Propylene Glycol and Diazolidinylurea (and) Methylparaben (and) Polyparaben (Germaben II, ISP Sutton) | 0–2.0 |
| Sodium PCA | 0–0.75 |
| Polyglyceryl Methacrylate (Lubrajel Oil, Amerchol) | 0–0.75 |
| A hydroxyethyl methacrylate homopolymer solution | 0–0.75 |

40. The skin tautening aqueous gel of claim 1 wherein the blend contains the following formulation:

| | Percent by weight: |
|---|---|
| Deionized Water | 69.84 |
| Hydroxyethyl Cellulose | 0.70 |
| A protein complex of Pea (*Pisum sativum*) and Sclerotium Gum | 0.50 |
| Disodium EDTA | 0.24 |
| Glycerin | 10.00 |
| Butylene Glycol (and) Algae Extract | 5.00 |
| Polysaccharide (and) Casein Hydrolyzate | 5.00 |
| Sodium Hyaluronate (1%) | 5.00 |
| Polyacrylamide gelling agent | 1.00 |
| Dimethicone Copolyol Isostearate | 0.01 |
| PEG-20 Methyl Glucose Sesquistearate | 0.01 |
| Polysorbate 40 | 0.01 |
| Polysorbate 60 | 0.01 |
| Polypropylene Glycol | 0.01 |
| Green Floral Fragrance | 0.23 |
| Red dye (0.1% aq. sol.) | 0.10 |
| Saccharide Isomerate | 1.00 |
| Propylene Glycol and Diazolidinylurea (and) Methylparaben (and) Polyparaben | 1.00 |
| Sodium PCA | 0.23 |
| Polyglyceryl Methacrylate | 0.08 |
| A hydroxyethyl methacrylate homopolymer solution | 0.01 |

41. A method for skin tautening which comprises placing, on a skin surface, a small amount of a skin tautening aqueous gel containing a homogeneous blend of water, a dispersed finely particulate vegetable based tensor agent containing a protein-based complex of vegetable extract and polysaccharides, a polymeric gelling agent, a liquid hydrocarbon dispersing aid and a nonionic surfactant that maintains the dispersion of the liquid hydrocarbon dispersing aid in the gel, and imbibing the gel into the skin surface.

* * * * *